United States Patent [19]

Roof et al.

[11] 4,301,401

[45] Nov. 17, 1981

[54] DIELECTRIC CONSTANT DETECTOR

[75] Inventors: Lewis B. Roof; L. V. Benningfield, Jr., both of Bartlesville, Okla.

[73] Assignee: Phillips Petroleum Co., Bartlesville, Okla.

[21] Appl. No.: 76,709

[22] Filed: Sep. 18, 1979

[51] Int. Cl.³ .......................................... G01R 27/26
[52] U.S. Cl. .............................. 324/61 R; 73/61.1 C; 73/23.1; 324/140 R
[58] Field of Search ................... 324/61 R, 140 R; 73/61.1 C, 23.1; 361/281, 278, 285, 292, 295, 299, 300

[56] References Cited

U.S. PATENT DOCUMENTS

| | | | |
|---|---|---|---|
| 2,485,579 | 10/1949 | Elliott | 324/61 R |
| 2,623,928 | 12/1952 | Bower | 324/61 R |
| 2,855,550 | 10/1958 | Bayha | 361/292 X |
| 3,096,591 | 7/1963 | Higgins, Jr. et al. | 324/61 R X |
| 3,405,333 | 10/1968 | Tilton | 361/295 X |
| 3,437,927 | 4/1969 | Cornwell, Jr. et al. | 324/102 |
| 3,482,153 | 12/1969 | Caprio | 361/295 |
| 3,523,245 | 8/1970 | Love et al. | 324/61 R |
| 3,715,657 | 2/1973 | Sampson | 73/23.1 X |
| 4,227,182 | 10/1980 | Ogasawara et al. | 324/61 R X |

FOREIGN PATENT DOCUMENTS 1279984  6/1972  United Kingdom ............ 324/61 R

OTHER PUBLICATIONS

Vespalec et al, Performance of the Capacitance Detector for Liquid Chromatography, Journal of Chromatography, vol. 65, pp. 53–69, 1972.

Benningfield, Jr., A Dielectric Constant Detector for Liquid Chromatography and Its Application, Mar. 5, 1979.

*Primary Examiner*—Stanley T. Krawczewicz

[57] ABSTRACT

A dielectric constant detector, having a sample cell and a reference cell, is provided which is useful to provide an electrical signal that is proportional to the concentration of a component being passed through the dielectric constant detector. The fluid to be analyzed together with a reference fluid is provided to the sample cell while only the reference fluid is provided to the reference cell. The difference in the capacitances of the two cells is utilized to determine the concentration of a component passing through the sample cell. The sample and reference cells are adjusted in such a manner that the capacitance of each cell is substantially equal when the same fluid is in both cells so as to substantially reduce the signal-to-noise ratios for the dielectric constant detector.

25 Claims, 3 Drawing Figures

DIELECTRIC CONSTANT DETECTOR

This invention relates to a dielectric constant detector. In one aspect this invention relates to method and apparatus for substantially matching the capacitance of the sample and reference cells of a dielectric constant detector.

The background, brief description and detailed description of the present invention are set forth in terms of the applicability of a dielectric constant detector to liquid chromatography. However, the present invention provides an improved dielectric constant detector which may be used in applications other than liquid chromatography.

A chromatographic analyzer is an analytical instrument that is used to separate in time and individually detect the constituents of a sample to be analyzed. The chromatographic analyzer typically includes an analytical column through which a carrier fluid is passed continuously. The sample to be analyzed is injected into the carrier stream and is thus carried through the analytical column. The sample constituents are carried through the analytical column at different velocities and in this manner the sample constituents are separated in time. A detector is employed to detect the separated constituents and the detector output signal typically is plotted as a function of time to produce what is termed a chromatogram. As each sample component is eluted from the column, the component produces a sharp increase in the detector output signal amplitude, which increase appears as a spike or peak in the chromatogram.

Several detectors are available which may be utilized in liquid chromatography to provide an electrical signal that is proportional to the concentration of the sample constituents being eluted from the chromatographic column. The two most widely used detectors are currently the ultraviolet absorption detector and the refractive index detector. The ultraviolet absorption detector is the more sensitive of the two, but is limited to substances that absorb ultraviolet radiation at the particular wavelength being utilized. Not all substances exhibit sufficient absorption at available wavelengths for the ultraviolet detector to be useful. In contrast, the refractive index detector is a universal detector in the sense that all substances possess a refractive index that in theory can be detected unless the solvent and solute have identical refractive indices. However, the relative difference between the refractive indexes for many solvent/solute systems is very small and for these systems it is very difficult to obtain any meaningful data utilizing a refractive index detector. Other liquid chromatography detectors such as electrical conductivity, fluorescence, radioactivity, and infra-red absorption detectors are available but these detectors have limited use due to their specificity.

The desirability of being able to use a detector which was dependent upon the dielectric constant as a detector for liquid chromatography has been recognized in the past. Like the refractive index detector, the dielectric constant detector is a universal detector since it responds to a change in a bulk property of the carrier as the solute elutes from the column. This measurement principle is attractive in comparison with refractive index measurements because the relative differences in the dielectric constants of various substances are generally much larger than the relative differences in refractive indices. Modern refractive index detectors are capable of detecting refractive index changes as small as 0.1 parts per million. The dielectric constant detector of the present invention is capable of detecting dielectric constant changes of 0.5 parts per million. Thus, the refractive index detector is more sensitive than the dielectric constant detector for solvent/solute systems where the relative differences in the refractive indices and the dielectric constants are approximately equal. However, there are many practical solvent/solute systems where the dielectric constant detector has a definite advantage over the refractive index detector. The dielectric constant detector is particularly useful if the sample components have approximately equal dielectric constants which is the case for non-polar hydrocarbons. By choosing a carrier that has a much higher dielectric constant, the sensitivity for each component is approximately equal and all the peaks are positive. This is rarely the case for a refractive index detector.

The primary problem which has prevented the development of a dielectric constant detector useful for liquid chromatography has been the matching of the capacitance of the sample cell and reference cell of the dielectric constant detector so as to provide a signal-to-noise ratio for the dielectric constant detector which is acceptable. The noise may be caused by a failure to match the capacitance of the sample cell and reference cell when manufacturing the dielectric constant detector or may be produced by physical movements of the components of the sample cell and reference cell so as to cause the capacitance of the sample cell and reference cell to become unmatched.

It is thus an object of this invention to provide a dielectric constant detector. It is one object of this invention to provide method and apparatus for substantially matching the capacitance of the sample and reference cells of a dielectric constant detector and insuring that the sample and reference cells will remain substantially matched.

In accordance with the present invention, method and apparatus is provided whereby a dielectric constant detector is utilized to provide an output which is representative of the concentration of components of a sample being passed through the sample cell of the dielectric constant detector. The reference and sample cells of the dielectric constant detector have first and second plates. The distance separating the first and second plates of either the reference cell or the sample cell or both the reference cell and the sample cell is not a constant. The first and second plates which are separated by a non-constant distance can be translated with respect to each other in order to substantially match the capacitance of the sample cell and the capacitance of the reference cell when the same fluid is flowing through both the sample cell and reference cell.

Once the capacitance of the sample cell and reference cell have been substantially matched, a reference fluid containing individual components of the sample is provided to the sample cell. At the same time reference fluid only is provided to the reference cell. Electronic circuitry associated with the sample cell provides an output signal having a frequency which is a function of the capacitance of the sample cell when the reference fluid plus sample fluid is flowing through the sample cell. Electronic circuitry associated with the reference cell also provides an output signal which has a frequency which is a function of the capacitance of the reference cell when only the reference fluid is flowing through the reference cell. The two output signals are mixed to provide a difference frequency and the difference frequency is converted to a voltage to provide an electrical signal which is representative of the concentration of the particular component of the sample which is passing through the dielectric constant detector.

Other objects and advantages of the invention will be apparent from the foregoing brief description of the invention and the appended claims as well as from the detailed description of the drawings in which:

The invention is described in terms of use of the dielectric constant detector in a specific chromatographic analyzer system. The invention is, however, applicable to use of the dielectric constant detector to other chromatographic analyzer systems and configurations. The dielectric constant detector may also be used in applications other than chromatography. It is also noted that the invention is described in terms of a specific mechanical configuration for the dielectric constant detector. However, the invention is not limited to the specific preferred mechanical configuration but is rather applicable to any mechanical configuration which accomplishes the purpose of the present invention.

Figure 1:
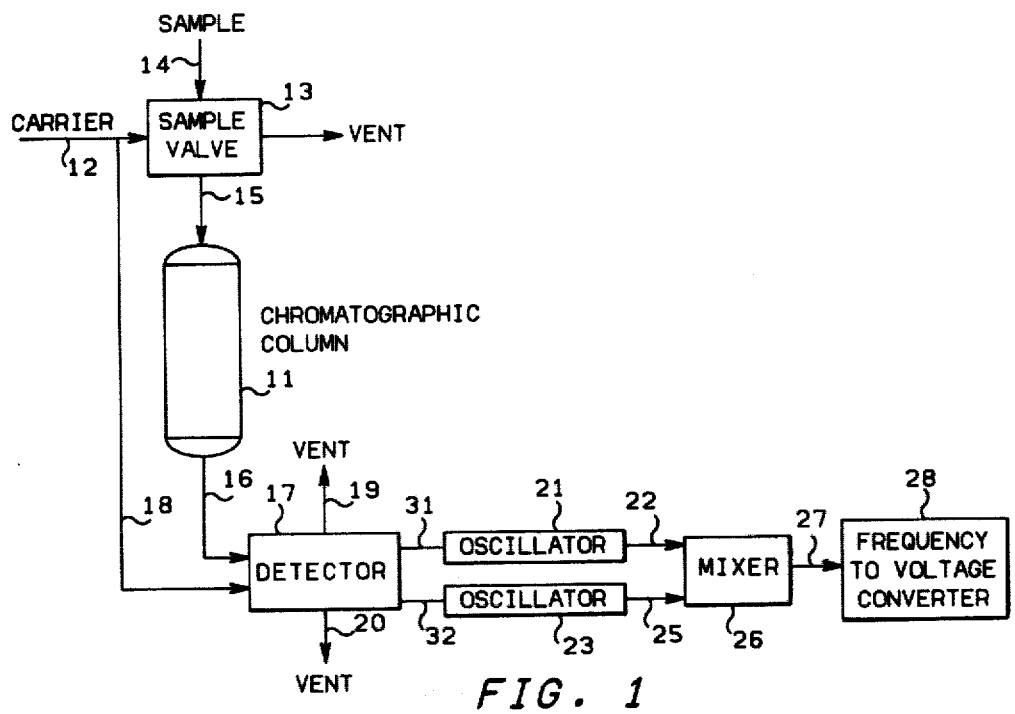
FIG. 1 is a representation of a chromatographic analyzer system employing a dielectric constant detector.

Referring now to the drawings and in particular to FIG. 1, there is illustrated a chromatographic column 11. A sample of a fluid to be analyzed is delivered to sample valve 13 through conduit means 14. Conduit means 15 extends between sample valve 13 and the chromatographic column 11. Conduit means 16 extends between the outlet of chromatographic column 11 and the sample inlet of the dielectric constant detector 17. Carrier fluid is passed through the reference portion of the dielectric constant detector 17 by being introduced into the reference inlet of the dielectric constant detector 17 through conduit means 18 which is in fluid communication with conduit means 12. Carrier fluid flows through sample valve 13 and chromatographic column 11 to the sample inlet of the dielectric constant detector 17. At the beginning of an analysis period, sample valve 13 is actuated to introduce a predetermined volume of sample into the carrier fluid flowing through chromatographic column 11. The constituents of the sample are eluted in sequence and flow from the chromatographic column 11 through conduit means 16 to the sample cell of the dielectric constant detector 17. An electrical conductor 31 electrically connects one plate of the sample cell to the oscillator 21. An electrical conductor 32 electrically connects one plate of the reference cell to the oscillator 23. The sample cell of the dielectric constant detector 17 in conjunction with the oscillator 21 establishes an output signal 22 which has a frequency which corresponds to the capacitance of the sample cell when a particular constituent of the sample is passing through the sample cell. In like manner, the reference cell of the dielectric constant detector 17 in conjunction with the oscillator 23 provides an output signal 25 which has a frequency which is a function of the capacitance of the reference cell when only carrier fluid is passing through the reference cell. Signal 22 is provided from the oscillator 21 as an input signal to the mixer 26. Signal 25 is provided from the oscillator 23 as an input to the mixer 26. Signals 22 and 25 are combined in the mixer 26 to provide signal 27 which is representative of the difference between the frequencies of signals 22 and 25. Signal 27 is provided from the mixer 26 as an input to the frequency-to-voltage converter 28. Signal 27 is converted from an oscillating signal to a DC voltage by the frequency-to-voltage converter 28 and the DC voltage will be representative of the concentration of the particular component passing through the sample cell.

Figure 2:
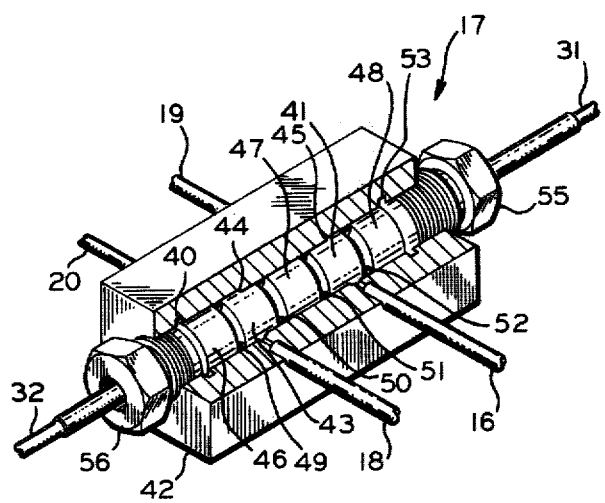
FIG. 2 is a detailed illustration of the dielectric constant detector illustrated in FIG. 1.

The dielectric constant detector 17 is more fully illustrated in FIG. 2. Referring now to FIG. 2, the sample cell of the dielectric constant detector 17 is formed by the center plate 41 and the outer plate 42. The reference cell is formed by the center plate 43 and the outer plate 42. All of the plates are preferably formed from stainless steel. The outer plate 42, which is common to both the sample cell and the reference cell, is preferably machined in the form of a prism having a substantially square transverse cross section. An opening extends for the length of the prism. The opening extending through the center portion of the prism forms first, second and third serially contiguously connected cylindrical openings. The first cylindrical opening extends from the edge of the groove 40 which is adjacent the spacer 46 to a circular line 44 which lies in a plane which is at least substantially perpendicular to the longitudinal axis of the opening, the plane extending through the longitudinal midregion of center plate 43. In the illustrated embodiment line 44 is formed by an annular shoulder. The second cylindrical opening extends from the line 44 to a circular line 45 which lies in a plane which is at least substantially perpendicular to the longitudinal axis of the opening, the plane extending through the longitudinal midregion of center plate 41. In the illustrated embodiment line 43 is formed by an annular shoulder. The third cylindrical opening extends from the line 45 to the edge of the groove 53 which is adjacent the spacer 48. The diameter of the first and third cylindrical openings are preferably equal. The diameter of the second cylindrical opening is less than the diameter of the first and third cylindrical openings. The center plates 41 and 43 do not touch the outer plate 42 at any point. The center plates 41 and 43 are cylindrical in form and are electrically isolated by the spacers 46, 47 and 48 which are preferably formed from KEL-F ® manufactured by Union Carbide. The O-rings 49–52, which are preferably Teflon ®, provide means for sealing the sample and reference cells to prevent leakage of fluid out of the sample and reference cells. The O-rings 49–52 also provide means for centering the center plates 41 and 43 with respect to the outer plate 42. The entire assembly consisting of the center plates 41 and 43, the spacers 46, 47 and 48 and the O-rings 49–52 is held in place by the end caps 55 and 56 which are coupled by means of threads to the outer plate 42. The end caps 55 and 56 also provide a means for longitudinally moving the center plates 41 and 43 with respect to the outer plate 42.

The electrical conductor 32 is electrically connected to the center plate 43 and is electrically isolated from the outer plate 42. The electrical conductor 31 is electrically connected to the center plate 41 and is electrically isolated from the outer plate 42. The outer plate 42 is electrically connected to ground.

The outer plate 42 and the center plate 41 form concentric cylindrical plates. Solute plus carrier is provided from the chromatographic column 11 through conduit means 16 to the space between the concentric cylindrical plates. All conduits are preferably 1/16 inch outside diameter × 0.010 inch inside diameter stainless steel tubing. The volume of the fluid which may be contained in the sample cell is determined by the position of the center plate 41 with respect to the outer plate 42. As has been previously noted, the second cylindrical opening in the outer plate 42, which extends into the sample cell, has a smaller diameter than the first cylindrical opening in the outer plate 42 which also extends into the sample cell. Longitudinal movement of the center plate 41 with respect to the outer plate 42 will thus change the volume of fluid which can be contained in the sample cell. The volume of fluid contained in the sample cell determines the capacitance of the sample cell and in this manner, the capacitance of the sample cell can be adjusted.

In like manner, carrier fluid is provided through conduit means 18 to the reference cell. The center plate 43 can be moved longitudinally along the common axis with respect to the outer plate 42 so as to adjust the capacitance of the reference cell in the same manner as previously described for the sample cell.

Movement of the center plate 41 and the center plate 43 is accomplished by simultaneously turning the end caps 55 and 56. Preferably, for purposes of adjustment only, carrier fluid only is provided to both the sample cell and the reference cell. The end caps 55 and 56 are then simultaneously turned so as to substantially match the capacitance of the sample cell and the capacitance of the reference cell when the same fluid is flowing through both cells.

With non-adjustable cells, the best match generally obtainable is about 5 percent. That is to say that one cell will have about 5 percent more capacitance than the other cell. With the adjustable cells of the present invention, the capacitance can be matched to 1/50 of 1 percent which presents an improvement of 200:1 over non-adjustable cells. This improvement results in a substantial improvement in the signal-to-noise performance of the dielectric constant detector.

It is again noted that the present invention is applicable to any mechanical configuration of the plates of the sample and reference cells so long as means is provided for changing the volume of fluid in the cells. Thus, parallel plate configurations or other desired plate configurations may be utilized if desired.

It is also noted that even though it is presently preferred to be able to vary the volume of fluid in both the sample and reference cells, it is only necessary that means be provided for varying the volume of fluid which can be contained in only one of the cells. Thus, the capacitance of one of the cells can be changed to match the capacitance of a cell which does not have means for adjusting the volume of fluid which can be contained in the cell.

Figure 3:
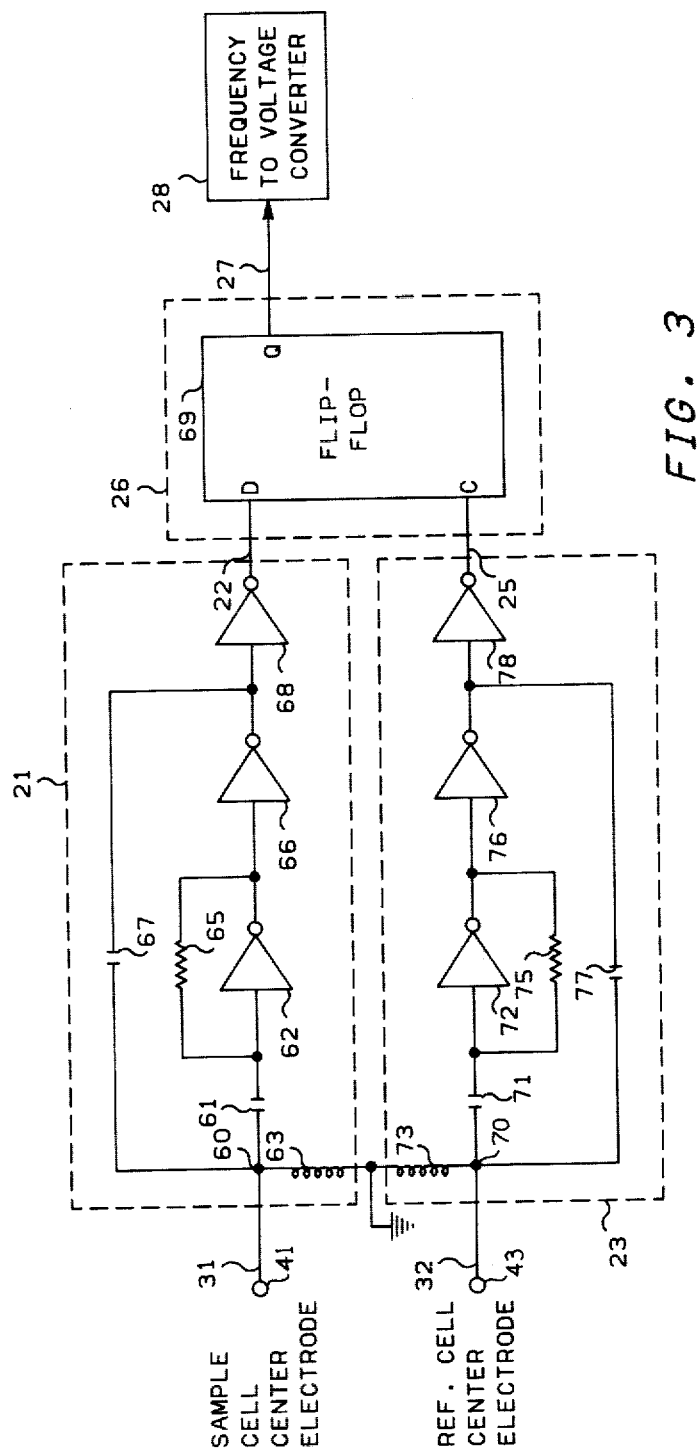
FIG. 3 is a schematic representation of the electrical circuitry illustrated in FIG. 1.

The oscillators 21 and 23 together with the mixer 26 and the frequency-to-voltage converter 28 illustrated in FIG. 1 are more fully illustrated in FIG. 3. Referring now to FIG. 3, the center plate 41 of the sample cell is electrically connected to node 60. The inductor 63 is electrically connected between node 60 and electrical ground. Node 60 and the input of the inverter 62 are electrically connected through the capacitor 61. The output of the inverter 62 is fed back to the input of the inverter 62 through resistor 65. The output of the inverter 62 is also electrically connected to the input of the inverter 66. The output of the inverter 66 is fed back to node 60 through capacitor 67. The output of the inverter 66 is also provided as an input to the inverter 68. The output of the inverter 68 forms signal 22 which has a frequency representative of the capacitance of the sample cell of the dielectric constant detector 17. Signal 22 is provided to the D input of the flip-flop 69 which forms the mixer 26 illustrated in FIG. 1.

The center plate 43 of the sample cell is electrically connected to node 70. The inductor 73 is electrically connected between node 70 and electrical ground. Node 70 and the input of the inverter 72 are electrically connected through the capacitor 71. The output of the inverter 72 is fed back to the input of the inverter 72 through resistor 75. The output of the inverter 72 is also electrically connected to the input of the inverter 76. The output of the inverter 76 is fed back to node 70 through capacitor 77. The output of the inverter 76 is also provided as an input to the inverter 78. The output of the inverter 78 forms signal 25 which has a frequency representative of the capacitance of the sample cell of the dielectric constant detector 17. Signal 25 is provided to the C input of the flip-flop 79 which forms the mixer 26 illustrated in FIG. 1.

The frequency of the output signal 22 from the sample oscillator 21 is determined primarily by the value of the inductor 63 and the capacitance of the sample cell of the dielectric constant detector 17. In like manner, the frequency of the output signal 25 from the reference oscillator 23 will be determined by the value of inductor 73 and the capacitance of the reference cell of the dielectric constant detector 17. The values of inductors 63 and 73 are preferably equal. Thus, the difference in the frequencies of signals 22 and 25 will be determined solely by the difference between the capacitance of the reference cell and the capacitance of the sample cell. The difference between the capacitance of the reference cell and the capacitance of the sample cell is determined by the dielectric constant of the component of the sample which together with the carrier fluid is flowing through the sample cell of the dielectric constant detector. Thus, the difference in the frequencies of signals 22 and 25 will be a function of the dielectric constant of the component of the sample which together with the carrier fluid is flowing through the sample cell of the dielectric constant detector.

The flip-flop 69 acts as a mixer. Thus, the Q output which is representative as signal 27 will be substantially equal to the difference in the frequencies of signals 22 and 25. Signal 27 is provided from the Q output of the flip-flop 69 to the frequency-to-voltage converter 28 which may be a Model 453J, K or L obtainable from Analog Device, Norwood, Mass. Signal 27 is converted from an AC signal to a DC voltage by the frequency-to-voltage converter 28 and the DC voltage will be proportional to the concentration of a component of the sample which is flowing through the sample cell of the dielectric constant detector 17.

Commercially available components plus the values for capacitors, inductors and resistors, which may be utilized in the circuit illustrated in FIG. 3 are as follows:

Inductors 63 and 73: 47 microhenries
Capacitors 61 and 71: 100 picofarads
Capacitors 67 and 77: 10 picofarads
Inverters 62, 66, 68, 72, 76 and 78: MC14049, Motorola Semiconductor
Resistors 65 and 75: 100 kohms
Flip-flop 69: MC14013, Motorola Semiconductor The invention has been described in terms of a preferred embodiment as illustrated in FIGS. 1-3. As has been previously stated, many different chromatographic analyzer configurations could be utilized and also many different electrical circuits could be utilized to process the output from the dielectric constant detector. In addition, mechanical variations which do not influence the operation of the dielectric constant detector are within the scope of the present invention. While the invention has been described in terms of the presently preferred embodiment, reasonable variations and modifications are possible by those skilled in the art within the scope of the described invention and the appended claims.

That which is claimed is:

1. A dielectric constant detector comprising:
   a reference cell having first and second plates which form a first capacitor;
   a sample cell having first and second plates which form a second capacitor;
   means for passing a fluid through said reference cell;
   means for passing a fluid through said sample cell; and
   means for substantially matching the capacitance of said first capacitor with the capacitance of said second capacitor when the same fluid is flowing through both said reference cell and said sample cell.

2. Apparatus in accordance with claim 1 wherein said means for substantially matching the capacitance of said first capacitor with the capacitance of said second capacitor comprises means for varying the volume of fluid which can be present between the first and second plates of at least one of said first capacitor and said second capacitor.

3. Apparatus in accordance with claim 1 wherein said means for substantially matching the capacitance of said first capacitor with the capacitance of said second capacitor comprises:
   means for varying the volume of fluid which can be present between the first and second plate of said first capacitor; and
   means for varying the volume of fluid which can be present between the first and second plates of said second capacitor.

4. A dielectric constant detector comprising:
   an outer plate having an opening extending through at least a portion of said outer plate, said opening forming at least first, second and third cylindrical openings;
   a first inner plate concentric with the portion of said outer plate which encloses a portion of said first cylindrical opening and a portion of said second cylindrical opening, said first inner plate and the portion of said outer plate with which said first inner plate is concentric forming a sample cell;
   a second inner plate concentric with the portion of said outer plate which encloses a portion of said second cylindrical opening and a portion of said third cylindrical opening, said second inner plate and the portion of said outer plate with which said second inner plate is concentric forming a reference cell;
   means for providing a fluid to said sample cell;
   means for providing a fluid to said reference cell;
   a first end cap located at the first end of said outer plate and operably coupled to said outer plate in such a manner that said first end cap may be moved into or out of said opening;
   a second end cap located at the second end of said outer plate and operably coupled to said outer plate in such a manner that said second end cap may be moved into or out of said opening, movement of said first end cap and said second end cap effecting movement of said first and second inner plates so as to provide means for substantially matching the capacitance of said sample cell and the capacitance of said reference cell when the same fluid is provided to both said reference cell and said sample cell.

5. A dielectric constant detector in accordance with claim 4 wherein said outer plate is a prism having a substantially square transverse cross section, said opening extending completely through the central portion of said prism and having a longitudinal axis which is substantially perpendicular to said substantially square transverse cross section.

6. A dielectric constant detector in accordance with claim 5 wherein the diameter of said first cylindrical opening is substantially equal to the diameter of said third cylindrical opening and the diameter of said second cylindrical opening is less than the diameter of said first cylindrical opening.

7. A dielectric constant detector in accordance with claim 6 additionally comprising:
   a first electrically insulating spacer operably located between said first inner plate and said second inner plate;
   a second electrically insulating spacer operably located between said first inner plate and said first end cap; and
   a third electrically insulating spacer operably located between said second inner plate and said second end cap.

8. A dielectric constant detector in accordance with claim 7 additionally comprising:
   first and second O-rings operably located so as to support said first inner plate and seal said sample cell to prevent fluid leakage from said sample cell; and
   third and fourth O-rings operably located so as to support said second inner plate and seal said reference cell to prevent fluid leakage from said reference cell.

9. A dielectric constant detector in accordance with claim 8 wherein said outer plate is electrically grounded.

10. A dielectric constant detector in accordance with claim 9 wherein said first inner plate is electrically connected to a first oscillator circuit and said second inner plate is electrically connected to a second oscillator circuit.

11. A dielectric constant detector in accordance with claim 10 wherein said first end cap is threaded into the first end of said outer plate and said second end cap is threaded into the second end of said outer plate.

12. Apparatus for obtaining an analysis of the concentration of a component of a material comprising:
   a chromatographic separation column means;
   means for passing a stream of a carrier fluid to said chromatographic separation column means;
   means for injecting a sample of said material into said stream of said carrier fluid flowing to said chromatographic separation column means;
   a dielectric constant detector means having a sample cell and a reference cell;
   means for adjusting the capacitance of at least one of said sample cell and said reference cell in such a manner that the capacitance of said sample cell is substantially equal to the capacitance of said reference cell when only said carrier fluid is flowing through both said reference cell and said sample cell;

means for passing the stream of said carrier fluid containing separated components of the sample of said material from said chromatographic separation column means through said sample cell of said dielectric constant detector means; and means for passing a stream of said carrier fluid through said reference cell of said dielectric detector means, the difference between the capacitance of said sample cell and the capacitance of said reference cell being representative of the concentration of a component of said sample passing through said sample cell.

13. Apparatus in accordance with claim 12 additionally comprising:

a first oscillator, said sample cell forming a capacitance element of said first oscillator, the output signal from said first oscillator having a frequency which is a function of the capacitance of said sample cell when the portion of said stream of said carrier fluid containing said component passes through said sample cell;

a second oscillator, said reference cell forming a capacitive element of said second oscillator, the output signal from said second oscillator having a frequency which is a function of the capacitance of said reference cell when the reference stream of said carrier fluid is passing through said reference cell;

means for combining the output signal from said first oscillator and the output signal from said second oscillator to establish a difference frequency signal; and means for converting said difference frequency signal to a DC voltage, said DC voltage being representative of the concentration of said component of said sample passing through said sample cell.

14. Apparatus in accordance with claim 12 wherein said means for adjusting the capacitance of at least one of said sample cell and said reference cell comprises means for varying the volume of fluid which can be present in said sample cell to thereby match the capacitance of said sample cell to the capacitance of said reference cell.

15. Apparatus in accordance with claim 12 wherein said means for adjusting the capacitance of at least one of said sample cell and said reference cell comprises means for varying the volume of fluid which can be present in said reference cell to thereby substantially match the capacitance of said reference cell with the capacitance of said sample cell.

16. Apparatus in accordance with claim 12 wherein said means for adjusting the capacitance of at least one of said sample cell and said reference cell comprises means for varying the volume of fluid which can be present in both said sample cell and said reference cell to thereby substantially match the capacitance of said sample cell and the capacitance of said reference cell.

17. A method for obtaining an analysis of the concentration of a component of a material comprising the steps of:

passing a stream of a carrier fluid to a chromatographic separation column means;

injecting a sample of said material into said stream of said carrier fluid flowing to said chromatographic separation column means;

adjusting the capacitance of at least one of the sample cell of a dielectric constant detector means and the reference cell of said dielectric constant detector means in such a manner that the capacitance of said sample cell is substantially equal to the capacitance of said reference cell when only said carrier fluid is flowing through both said reference cell and said sample cell;

passing the stream of said carrier fluid containing separated components of the sample of said material from said chromatographic separation column means through said sample cell of said dielectric constant detector means; and passing a stream of said carrier fluid through said reference cell of said dielectric detector means, the difference between the capacitance of said sample cell and the capacitance of said reference cell being representative of the concentration of a component of said sample passing through said sample cell.

18. A method in accordance with claim 17 additionally comprising the steps of:

generating a first output signal having a frequency which is a function of the capacitance of said sample cell when the portion of said stream of said carrier fluid containing said component passes through said sample cell;

generating a second output signal which has a frequency which is a function of the capacitance of said reference cell when the reference stream of said carrier fluid is passing through said reference cell;

combining said first output signal and said second output signal to establish a difference frequency signal; and converting said difference frequency signal to a DC voltage, said DC voltage being representative of the concentration of said component of said sample passing through said sample cell.

19. A method in accordance with claim 17 wherein said step of adjusting the capacitance of at least one of said sample cell and said reference cell comprises varying the volume of fluid which can be present in said sample cell to thereby match the capacitance of said sample cell to the capacitance of said reference cell.

20. A method in accordance with claim 17 wherein said step of adjusting the capacitance of at least one of said sample cell and said reference cell comprises varying the volume of fluid which can be present in said reference cell to thereby substantially match the capacitance of said reference cell with the capacitance of said sample cell.

21. A method in accordance with claim 17 wherein said step of adjusting the capacitance of at least one of said sample cell and said reference cell comprises varying the volume of fluid which can be present in both said sample cell and said reference cell to thereby substantially match the capacitance of said sample cell and the capacitance of said reference cell.

22. A method for improving the signal-to-noise ratio of a dielectric constant detector comprising the step of adjusting the capacitance of at least one of the sample cell of said dielectric constant detector and the reference cell of said dielectric constant detector in such a manner that the capacitance of said sample cell is substantially equal to the capacitance of said reference cell when the same fluid is flowing through both said reference cell and said sample cell.

23. A method in accordance with claim 22 wherein said step of substantially matching the capacitance of said sample cell with the capacitance of said reference cell comprises varying the volume of fluid which can be present in said sample cell to thereby match the capacitance of said sample cell to the capacitance of said reference cell.

24. A method in accordance with claim 22 wherein said step of substantially matching the capacitance of said sample cell with the capacitance of said reference cell comprises varying the volume of fluid capacitance of said reference cell comprises varying the volume of fluid which can be present in said reference cell to thereby substantially match the capacitance of said reference cell with the capacitance of said sample cell.

25. A method in accordance with claim 22 wherein said step of substantially matching the capacitance of said sample cell with the capacitance of said reference cell comprises varying the volume of fluid which can be present in both said sample cell and said reference cell to thereby substantially match the capacitance of said sample cell and the capacitance of said reference cell.

* * * * *